United States Patent
Baer et al.

(10) Patent No.: US 7,075,640 B2
(45) Date of Patent: Jul. 11, 2006

(54) CONSUMABLE FOR LASER CAPTURE MICRODISSECTION

(75) Inventors: Thomas M. Baer, Mountain View, CA (US); David F. Head, Los Gatos, CA (US); John Toeppen, Livermore, CA (US)

(73) Assignee: Arcturus Bioscience, Inc., Mountain View, CA (US)

( * ) Notice: Subject to any disclaimer, the term of this patent is extended or adjusted under 35 U.S.C. 154(b) by 0 days.

(21) Appl. No.: 08/984,979

(22) Filed: Dec. 4, 1997

(65) Prior Publication Data

US 2001/0038449 A1    Nov. 8, 2001

Related U.S. Application Data

(60) Provisional application No. 60/060,732, filed on Oct. 1, 1997.

(51) Int. Cl.
*G01N 21/01* (2006.01)
(52) U.S. Cl. ................................... 356/244
(58) Field of Classification Search ........ 356/244–246; 428/329, 447, 452, 332, 339, 346, 352; 422/102, 422/55–58, 61; 436/163, 101, 103, 84, 110, 436/113, 813, 174, 175, 177; 156/99, 108, 156/246, 285, 289, 308.2, 309.6; 435/40.5, 435/6, 7.21, 7.23, 40.52, 4, 29, 7.29, 174, 435/156, 157, 100
See application file for complete search history.

(56) References Cited

U.S. PATENT DOCUMENTS

| | | | |
|---|---|---|---|
| 2,801,568 A | 8/1957 | Dakin | |
| 3,680,947 A | 8/1972 | Wanesky | 350/81 |
| 3,684,099 A * | 8/1972 | Kiebach | |
| 3,705,769 A | 12/1972 | Johannsmeier | 355/91 |
| 3,836,231 A | 9/1974 | Cole, Jr. | |
| 3,848,962 A | 11/1974 | Nelson | 350/86 |
| 3,939,019 A | 2/1976 | Pickett | |
| 3,995,941 A * | 12/1976 | Nagahara et al. | |
| 4,064,205 A | 12/1977 | Landsman | |
| 4,080,476 A | 3/1978 | Laskey | |
| 4,149,803 A | 4/1979 | Litz | |
| 4,205,059 A | 5/1980 | von Hagens | |
| 4,210,384 A | 7/1980 | Meyer et al. | 350/19 |
| 4,245,003 A | 1/1981 | Oransky et al. | |
| 4,302,480 A | 11/1981 | Fischer et al. | |
| 4,303,866 A | 12/1981 | Porro et al. | 250/442 |

(Continued)

FOREIGN PATENT DOCUMENTS

CH         566 015 A         8/1975

(Continued)

OTHER PUBLICATIONS

Emmert-Buck, M. et al., "Laser Capture Microdissection", *Science*, vol. 274, Nov. 8, 1996, pp. 998-1001.

(Continued)

*Primary Examiner*—Tu T. Nguyen
(74) *Attorney, Agent, or Firm*—Lukas IP Group; Rimas T. Lukas

(57) ABSTRACT

Systems and methods for acquiring laser capture microdissection samples are disclosed. An integral portion of a biological reaction vessel includes a transfer film carrier having a substrate surface; and a laser capture microdissection transfer film coupled to the substrate surface of the transfer film carrier. The systems and methods facilitate quick and accurate laser capture microdissection while simultaneously minimizing contamination.

76 Claims, 9 Drawing Sheets

U.S. PATENT DOCUMENTS

| | | | |
|---|---|---|---|
| 4,320,157 A | 3/1982 | Von Hagens | |
| 4,333,983 A | 6/1982 | Allen | |
| 4,436,385 A | 3/1984 | Fischer et al. | 350/529 |
| 4,467,915 A | 8/1984 | Snyder et al. | |
| 4,497,792 A | 2/1985 | Gindler | |
| 4,508,435 A | 4/1985 | Graham et al. | 350/529 |
| 4,509,834 A | 4/1985 | Hodgson | 350/521 |
| 4,538,885 A | 9/1985 | Graham et al. | 350/529 |
| 4,552,033 A | 11/1985 | Marzhauser | 74/479 |
| 4,588,579 A | 5/1986 | Bachhuber et al. | |
| 4,588,674 A | 5/1986 | Stewart et al. | |
| 4,600,282 A | 7/1986 | Yamamura et al. | 353/122 |
| 4,614,431 A | 9/1986 | Komeyama | 356/401 |
| 4,624,915 A | 11/1986 | Schindler et al. | |
| 4,627,009 A | 12/1986 | Holmes et al. | 364/559 |
| 4,629,687 A | 12/1986 | Schindler et al. | |
| 4,673,261 A | 6/1987 | Hunt et al. | 350/531 |
| 4,684,781 A | 8/1987 | Frish et al. | |
| 4,702,565 A | 10/1987 | Schilling et al. | 350/531 |
| 4,731,530 A | 3/1988 | Mikan | 250/229 |
| 4,743,463 A | 5/1988 | Ronn et al. | |
| 4,752,455 A | 6/1988 | Mayer | |
| 4,756,922 A | 7/1988 | Motoyama et al. | |
| 4,784,873 A | 11/1988 | Kienecker et al. | |
| 4,807,984 A | 2/1989 | Kurimura et al. | 350/529 |
| 4,824,229 A | 4/1989 | Narita et al. | 350/531 |
| 4,836,667 A | 6/1989 | Ozeki | 350/531 |
| 4,839,194 A | 6/1989 | Malluche et al. | |
| 4,852,985 A | 8/1989 | Fujihara et al. | 350/523 |
| 4,856,873 A | 8/1989 | Kleinberg | 350/502 |
| 4,871,245 A | 10/1989 | Ishikawa et al. | 350/502 |
| 4,895,735 A | 1/1990 | Cook | |
| 4,906,494 A | 3/1990 | Babinec et al. | |
| 4,911,782 A | 3/1990 | Brown | |
| 4,920,053 A | 4/1990 | Inoue et al. | 435/240.1 |
| 4,923,294 A | 5/1990 | Courtenay | 350/529 |
| 4,954,715 A | 9/1990 | Zöld | |
| 4,964,708 A | 10/1990 | Mason | 350/519 |
| 4,987,006 A | 1/1991 | Williams et al. | |
| 4,992,660 A | 2/1991 | Kobayashi | 250/306 |
| 5,017,428 A | 5/1991 | Mecke et al. | |
| 5,023,187 A | 6/1991 | Koebler et al. | |
| 5,029,791 A | 7/1991 | Ceccon et al. | 248/287 |
| 5,057,689 A | 10/1991 | Nomura et al. | 250/310 |
| 5,077,620 A | 12/1991 | Mauro | 359/393 |
| 5,089,909 A | 2/1992 | Kleinberg | 359/363 |
| 5,103,338 A | 4/1992 | Crowley et al. | 359/394 |
| 5,126,877 A | 6/1992 | Biber | 359/389 |
| 5,132,129 A | 7/1992 | Potter et al. | |
| 5,143,552 A | 9/1992 | Moriyama | |
| 5,158,895 A | 10/1992 | Ashihara et al. | |
| 5,162,941 A | 11/1992 | Favro et al. | 359/386 |
| 5,165,297 A | 11/1992 | Krueger | 74/479 |
| 5,173,802 A | 12/1992 | Heller | 359/384 |
| 5,173,803 A | 12/1992 | Heller | 359/384 |
| 5,192,503 A | 3/1993 | McGrath et al. | |
| 5,202,230 A | 4/1993 | Kamentsky | |
| 5,217,768 A | 6/1993 | Walters et al. | |
| 5,221,698 A | 6/1993 | Amidon et al. | |
| 5,225,326 A | 7/1993 | Bresser et al. | |
| 5,253,110 A | 10/1993 | Ichihara et al. | 359/619 |
| 5,262,891 A | 11/1993 | Nakasato | 359/385 |
| 5,263,384 A | 11/1993 | Suzuki | 74/479 MF |
| 5,280,384 A | 1/1994 | Shibasaki | |
| 5,288,996 A | 2/1994 | Betzig et al. | 250/227.26 |
| 5,292,559 A | 3/1994 | Joyce, Jr. et al. | |
| 5,296,291 A | 3/1994 | Mueller | |
| 5,296,963 A | 3/1994 | Murakami et al. | 359/389 |
| 5,300,540 A | 4/1994 | Masters | |
| 5,312,393 A | 5/1994 | Mastel | 606/4 |
| 5,323,009 A | 6/1994 | Harris | 250/458.1 |
| 5,337,178 A | 8/1994 | Kung et al. | 359/393 |
| 5,345,333 A | 9/1994 | Greenberg | 359/389 |
| 5,346,765 A | 9/1994 | Maeda et al. | |
| 5,349,436 A | 9/1994 | Fisch | |
| 5,357,366 A | 10/1994 | Marchlenski | 359/393 |
| 5,359,417 A | 10/1994 | Muller et al. | 356/375 |
| 5,367,401 A | 11/1994 | Saulietis | 359/398 |
| 5,378,675 A | 1/1995 | Takeyama et al. | |
| 5,386,112 A | 1/1995 | Dixon | 250/234 |
| 5,391,329 A | 2/1995 | Dougherty et al. | |
| 5,393,647 A | 2/1995 | Neukermans et al. | 430/320 |
| 5,403,970 A | 4/1995 | Aoki | 84/626 |
| 5,412,503 A | 5/1995 | Nederlof | 359/393 |
| 5,416,131 A | 5/1995 | Wolff et al. | |
| 5,420,716 A | 5/1995 | Fukaya | 359/368 |
| 5,427,950 A * | 6/1995 | Shigematsu et al. | 250/358.1 |
| 5,434,703 A | 7/1995 | Morizumi | 359/385 |
| 5,450,233 A | 9/1995 | Yamamoto et al. | 359/368 |
| 5,455,420 A | 10/1995 | Ho et al. | 250/306 |
| 5,468,967 A | 11/1995 | Chan et al. | 250/397 |
| 5,471,260 A | 11/1995 | Luce et al. | 351/205 |
| 5,479,252 A | 12/1995 | Worster et al. | 356/237 |
| 5,486,335 A | 1/1996 | Wilding et al. | |
| 5,492,837 A | 2/1996 | Naser-Kolahzadeh et al. | |
| 5,492,861 A | 2/1996 | Opower | |
| 5,493,861 A | 2/1996 | Friedrichsen | |
| 5,494,646 A | 2/1996 | Seymour | |
| 5,504,366 A | 4/1996 | Weiss et al. | 73/863 |
| 5,506,725 A | 4/1996 | Koike et al. | 359/388 |
| 5,510,615 A | 4/1996 | Ho et al. | 250/306 |
| 5,513,768 A | 5/1996 | Smith | |
| 5,517,353 A | 5/1996 | Ikoh et al. | 359/388 |
| 5,529,841 A | 6/1996 | Neihof | |
| 5,531,997 A | 7/1996 | Cochrum | |
| 5,532,128 A | 7/1996 | Eggers et al. | |
| 5,532,476 A | 7/1996 | Mikan | 250/221 |
| 5,532,873 A | 7/1996 | Dixon | 359/388 |
| 5,535,052 A | 7/1996 | Jorgens | 359/388 |
| 5,536,941 A | 7/1996 | Swann | 250/311 |
| 5,537,863 A | 7/1996 | Fujiu et al. | 73/105 |
| 5,541,064 A | 7/1996 | Bacus et al. | |
| 5,552,928 A | 9/1996 | Furuhashi et al. | 359/379 |
| 5,556,790 A | 9/1996 | Pettit | |
| 5,557,456 A | 9/1996 | Garner et al. | 359/393 |
| 5,558,329 A | 9/1996 | Liu | 273/148 B |
| 5,559,329 A | 9/1996 | Joseph et al. | 250/306 |
| 5,574,077 A | 11/1996 | Dougherty et al. | |
| 5,578,832 A | 11/1996 | Trulson et al. | |
| 5,580,612 A | 12/1996 | Hickel et al. | |
| 5,587,748 A | 12/1996 | Luce et al. | 351/208 |
| 5,587,833 A | 12/1996 | Kamentsky | 359/393 |
| 5,598,888 A | 2/1997 | Sullivan et al. | 165/263 |
| 5,602,674 A | 2/1997 | Weissman et al. | 359/393 |
| 5,619,035 A | 4/1997 | Weiss et al. | 250/306 |
| 5,621,207 A | 4/1997 | O'Mara | 250/221 |
| 5,621,619 A * | 4/1997 | Seffernick et al. | |
| 5,631,734 A | 5/1997 | Stern et al. | |
| 5,633,535 A * | 5/1997 | Chao et al. | |
| 5,638,206 A | 6/1997 | Sumiya et al. | 359/368 |
| 5,639,428 A | 6/1997 | Cottingham | |
| 5,641,896 A | 6/1997 | Karrai | 73/105 |
| 5,659,421 A | 8/1997 | Rahmel et al. | 359/391 |
| 5,665,582 A | 9/1997 | Kausch et al. | |
| 5,674,328 A | 10/1997 | Mannava et al. | |
| 5,686,313 A | 11/1997 | Sitte et al. | |
| 5,707,801 A | 1/1998 | Bresser et al. | |
| 5,723,290 A | 3/1998 | Eberwine et al. | |
| 5,728,527 A | 3/1998 | Singer et al. | |
| 5,751,839 A | 5/1998 | Drocourt et al. | |
| 5,756,049 A | 5/1998 | Brayton | |
| 5,759,781 A | 6/1998 | Ward et al. | |
| 5,763,191 A | 6/1998 | Knoll et al. | |
| 5,786,022 A | 7/1998 | Agarwal et al. | |

| | | |
|---|---|---|
| 5,812,312 A | 9/1998 | Lorincz |
| 5,817,462 A | 10/1998 | Garini et al. |
| 5,843,644 A | 12/1998 | Liotta et al. |
| 5,843,657 A * | 12/1998 | Liotta et al. ............... 156/57 |
| 5,859,699 A | 1/1999 | Baer et al. |
| 5,860,937 A | 1/1999 | Cohen |
| 5,912,134 A | 6/1999 | Shartle |
| 5,985,085 A | 11/1999 | Baer et al. |
| 6,010,888 A | 1/2000 | Liotta et al. |
| 6,100,051 A | 8/2000 | Goldstein et al. |
| 6,157,446 A | 12/2000 | Baer et al. |
| 6,184,973 B1 | 2/2001 | Baer et al. |
| 6,204,030 B1 | 3/2001 | Liotta et al. |
| 6,215,550 B1 | 4/2001 | Baer et al. |
| 6,251,467 B1 | 6/2001 | Liotta et al. |
| 6,251,516 B1 | 6/2001 | Bonner et al. |
| 6,277,648 B1 | 8/2001 | Colpan |
| 2001/0031481 A1 | 10/2001 | Liotta et al. |

FOREIGN PATENT DOCUMENTS

| | | |
|---|---|---|
| DE | 19 38 943 | 2/1971 |
| DE | 196 03 996 A1 | 8/1997 |
| EP | 0 081 976 A1 | 6/1983 |
| EP | 0 081 976 B1 | 6/1983 |
| EP | 0 388 168 | 9/1990 |
| EP | 0 409 550 A1 | 1/1991 |
| GB | 1 317 803 | 5/1973 |
| JP | 01330398 | 8/1991 |
| WO | WO91/07683 | 5/1991 |
| WO | WO 94/02646 A1 | 2/1994 |
| WO | WO95/23960 | 8/1995 |
| WO | WO 95 30919 | 11/1995 |
| WO | WO 95/30919 A1 | 11/1995 |
| WO | WO 96/16517 A1 | 5/1996 |
| WO | WO 96/40435 A1 | 12/1996 |
| WO | WO97/13838 | 4/1997 |
| WO | WO 97/13838 A1 | 4/1997 |
| WO | WO 97/29354 A1 | 8/1997 |
| WO | WO 98/35215 A1 | 8/1998 |
| WO | WO 98/36261 A1 | 8/1998 |
| WO | WO 9835215 | 8/1998 |
| WO | WO 9835216 A | 8/1998 |
| WO | WO 99/00658 A1 | 1/1999 |
| WO | WO 99/09390 A1 | 2/1999 |
| WO | WO 99/17094 A2 | 4/1999 |
| WO | WO 99/19341 A1 | 4/1999 |
| WO | WO 99/39176 A1 | 8/1999 |
| WO | WO 99/45094 A1 | 9/1999 |
| WO | WO 00/05587 A2 | 2/2000 |
| WO | WO 00/05587 A3 | 2/2000 |
| WO | WO 00/06992 A1 | 2/2000 |
| WO | WO 00/34756 A2 | 6/2000 |
| WO | WO 00/34756 A3 | 6/2000 |
| WO | WO 00/34757 A1 | 6/2000 |
| WO | WO 00/49410 A2 | 8/2000 |
| WO | WO 00/49410 A3 | 8/2000 |
| WO | WO 00/66994 A2 | 11/2000 |
| WO | WO 00/68662 A1 | 11/2000 |
| WO | WO 01/33190 A2 | 5/2001 |

OTHER PUBLICATIONS

Bielser, G. et al., "Cell surgery by laser micro-dissection: a preparative method", *Journal of Microscopy*, vol. 107, Pt. 1, May 1976, pp. 19-24.

Bonner, R. et al., "Laser Capture Microdissection: Molecular Analysis of Tissue", *Science*, vol. 278, Nov. 21, 1997, pp. 1481-1483.

Friend, T., "Getting up close to cancer genes", printed in *USA Today* newspaper, Science section, Aug. 5, 1997.

Schindler, M., "Select, microdissect, and eject", *Nature Biotechnology*, vol. 16, No. 8, Aug. 1998, pp. 719-720.

Schutze, K. et al., "Identification of expressed genes by laser-mediated manipulation of single cells", *Nature Biotechnology*, vol. 16, No. 8, Aug. 1998, pp. 737-742.

Meier-Ruge, W. et al., "The laser in the Lowry technique for microdissection of freeze-dried tissue slices", *Histochemical Journal*, vol. 8 (1976), pp. 387-401.

Kubo, Y. et al., "Early Detection of Knudson's Two-Hits in Preneoplastic Renal Cells of the Eker Rat Model by the Laser Microdissection Procedure", *Cancer Research*, vol. 55, No. 5, Mar. 1995, pp. 989-990.

Jimenez, C.R. et al., "Neuropeptide Expression and Processing as Revealed by Direct Matrix-Assisted Laser Desorption Ionization Mass Spectrometry of Single Neurons", *Journal of Neurochemistry*, vol. 62, No. 1, Jan. 1994, pp. 404-407.

Schindler, M. et al., Automated Analysis and Survival Selection of Anchorage-Dependent Cells Under Normal Growth Conditions, *Cytometry*, vol. 6, No. 4, Jul. 1985, pp. 368-374.

Fukui, K. et al., "Microdissection of plant chromosomes by argon-ion laser beam", *Theoretical and Applied Genetics*, vol. 84, No. 1-2, Jun. 1992, pp. 787-791.

Ashkin, A. et al., "Internal cell manipulation using infrared laser traps", *Proc. Natl. Acad. Sci. USA*, vol. 86, No. 20, Oct. 1989, pp. 7914-7918.

Veigel, C. et al., "New cell biological applications of the laser microbeam technique: the microdissection and skinning of muscle fibers and the perforation and fusion of sarcolemma vesicles", *European Journal of Cell Biology*, vol. 63, No. 1, Feb. 1994, pp. 140-148.

Geduspan, J. et al., "A Growth-Promoting Influence from the Mesonephros during Limb Outgrowth", *Developmental Biology*, vol. 151, No. 1, May 1992, pp. 242-250.

U.S. Appl. No. 08/800,882, filed Feb. 14, 1997, Baer et al.
U.S. Appl. No. 08/984,979, filed Dec. 4, 1997, Baer et al.
U.S. Appl. No. 09/018,452, filed Feb. 4, 1998, Baer et al.
U.S. Appl. No. 09/058,711, filed Apr. 10, 1998, Baer et al.
U.S. Appl. No. 09/121,635, filed Jul. 23, 1998, Baer et al.
U.S. Appl. No. 09/121,677, filed Jul. 23, 1998, Baer et al.
U.S. Appl. No. 09/121,691, filed Jul. 23, 1998, Baer et al.
U.S. Appl. No. 09/208,604, filed Dec. 8, 1998, Baer et al.
U.S. Appl. No. 09/344,612, filed Jun. 25, 1999, Baer et al.
U.S. Appl. No. 09/357,423, filed Jul. 20, 1999, Baer.
U.S. Appl. No. 09/538,862, filed Mar. 29, 2000, Baer et al.
U.S. Appl. No. 09/617,742, filed Jul. 17, 2000, Baer et al.
U.S. Appl. No. 09/706,332, filed Nov. 3, 2000, Baer et al.

Allred, D. C. and Mohsin, S. K. (2000). "Biological Features of Human Premalignant Breast Disease," Chapter 24 *In Disease of the Breast*, 2nd ed., J. R. Harris, ed., Lippicott Williams & Wilkins: Philadelphia, pp. 355-366.

Bentley-Lawrence, J. et al. (1988). "Sensitive, High-Resolution Chromatin and Chromosome Mapping In Situ: Presence and Orientation of Two Closely Integrated Copies of EBV in a Lymphoma Line," *Cell* 52:51-61.

Brignole, E. (Nov./Dec. 2000). "Laser-Capture Microdissection," pp. 1-5, located at <<http://pubs.acs.org/subscribe/journals/mdd/v03/i09/html/toolbox.html>> visted on Dec. 14, 2001 from *Modern Drug Discovery*, 3(9):69-70.

Chu, S. S. et al. (2000). "Laser Capture Microdissection: Applications in Cancer Research," *Biomedical Product* 2514p. 58:1-3.

Chui, G. (1999). "The Ecosystems Within" Section F, Science & Technology *San Jose Mercury News* pp. 1-5.

Friend, T. (1997). "Microdissection on Breakthrough Lets Scientists Isolate Those Involved in Tumor Growth," printed in *USA Today* Newspaper, Science Section, 2 pages.

Goldstein, S. R. et al. (Nov. 1, 1998). "Thermal Modeling of Laser Capture Microdissection," *Applied Optics* 37(31):7378-7391.

Goldsworthy, S. M. et al. (1999). "Effects of Fixation on RNA Extraction and Amplification from Laser Capture Microdissected Tissue" *Molecular Carcinogenesis* 25:86-91.

Harlow, E. and Lane, D. eds. (1988). *Antibodies: A Laboratory Manual* Cold Spring Harbor, New York: pp. iii-ix (Table of Contents Only).

Heng, H. H. Q. et al. (1992). "High-Resolution Mapping of Mammalian Genes by *In Situ* Hybridization to Free Chromatin," *Proc. Natl. Acad. Sci. USA* 89:9509-9513.

Kuska, B. (Dec. 4, 1996). "New Aim-and-Shoot Technique Speeds up Cell Analysis," *J. Natl. Cancer Inst.* 88(23):1708-1709.

Lewis, R. (1998). "Laser Aids Alzheimer's Study," *Biophotonics International* Nov./Dec.: 40-41.

Lichter, P. et al. (Jan. 1990). "High-Resolution Mapping of Human Chromosome 11 by *In Situ* Hybridization with Cosmid Clones," *Science* 247:64-69.

Manuelidis, L. et al. (Nov. 1982). "High-Resolution Mapping of Satellite DNA Using Biotin-Labeled DNA Probes," *The J. Cell. Biol.* 95:619-625.

Relman, D. A. (May 21, 1999). "The Search for Unrecognized Pathogens", *Science* 284:1308-1310.

van den Engh, Ger et al. (Sep. 4, 1992). "Estimating Genomic Distance from DNA Sequence Location in Cell Nuclei by a Random Walk Model," *Science* 257:1410-1412.

Anonymous. (Sep. 22, 1995). "Lazer Hazards," Section II, Chapter 6 *In OSHA Technical Manual*. United States Department of Labor Occupational Safety and Health Administration, pp. 6-1—6-40.

Berns et al. (Apr. 1998). "Laser Scissors and Tweezers," *Scientific America*, pp. 62-67.

Böhm, M. et al. (Jul. 1997). "Non-Contact Laser Microdissection of Membrane-Mounted Native Tissue," *Amer. J. of Pathol.* 151(1):63-67.

Burgemeister et al. (Mar. 13, 1998). "Laser Microdissection and Laser Pressure Catapulting: Genetic Analysis of Single Cells After Laser Microbeam Seperation: Trophoblastic Cells from Cervical Mucus and Fetal Erythroblasts from Maternal Blood," *P.A.L.M. Mikrolaser Technologies Workshop*, Abstract (1 page total).

Cremer, M. et al. (Mar. 25-28, 1998). "Collection of Individual Chromosomes and Nuclear Segments by Laser Microdissection and Laser Pressure Catapulting," *P.A.L.M. Mikrolaser Technologies Workshop*, Abstract (1 page total).

Isenberg, G. et al. (May 1976). "Cell Surgery by Laser Micro-Dissection: A Preperative Method," *Microscopy* 107(1):19-24.

Pontén, F. et al. (1997). "Genomic Analysis of Single Cells from Human Basal Cell Cancer Using Laser-Assisted Capture Microscopy," *Mutation Res. Genomics* 382:45-55.

Schütze et al. (1997). "Cut out or Poke in-The Key to the World of Single Genes: Laser Micromanipulation as a Valuable Tool on the Look-Out for the Origin of Disease," *Genetic Analysis: Biomolecular Engineering* 14:1-8.

Schütze, L. and Lahr, G. (May 1998). "Laser Microdissection and Laser Catapulting: A Key-Technique for Single Cell Based Gene Analysis," *BIOforum Int'l.*:177-180.

Simone, N.L. et al. (Jul. 1998). "Laser-Capture Microdissection: Opening the Microscopic Frontier to Molecular Analysis," *TIG* 14(7):272-276.

Thalhammer, S. et al. (Jan. 1997). "Laser Microdissection of Metaphase Chromosomes and Characterization by Atomic Force Microscopy," *J. Biomedical Optics* 2(1):115-119.

* cited by examiner

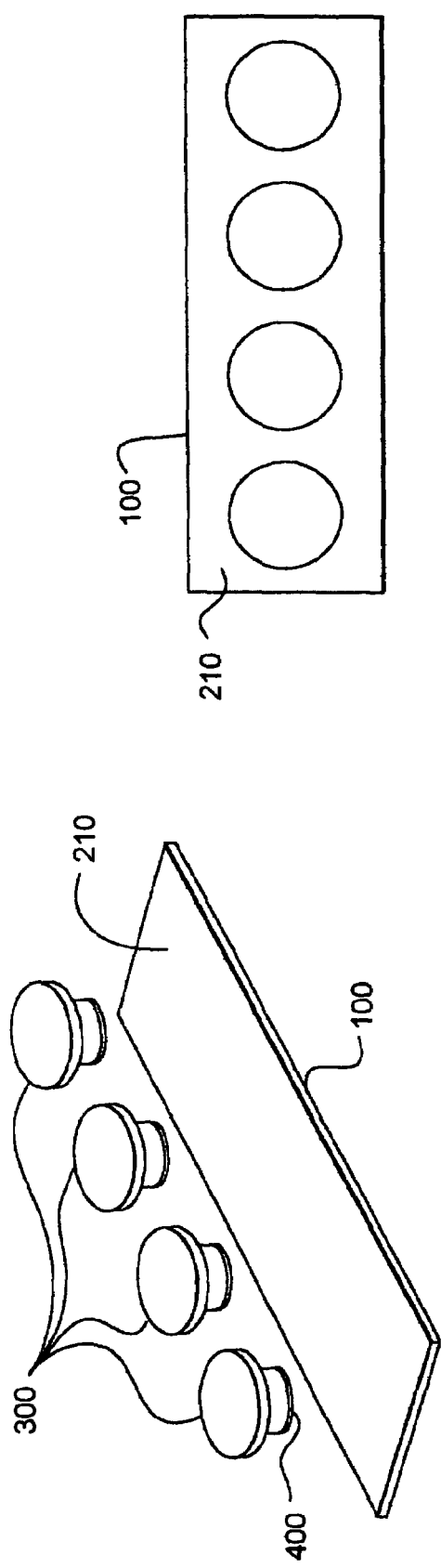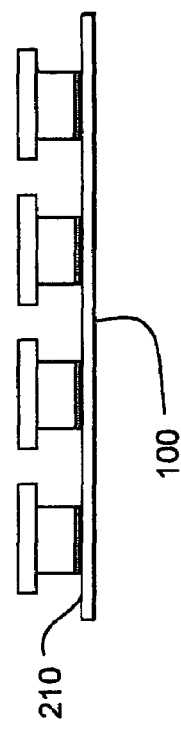
FIG. 5B
FIG. 5C
FIG. 5A

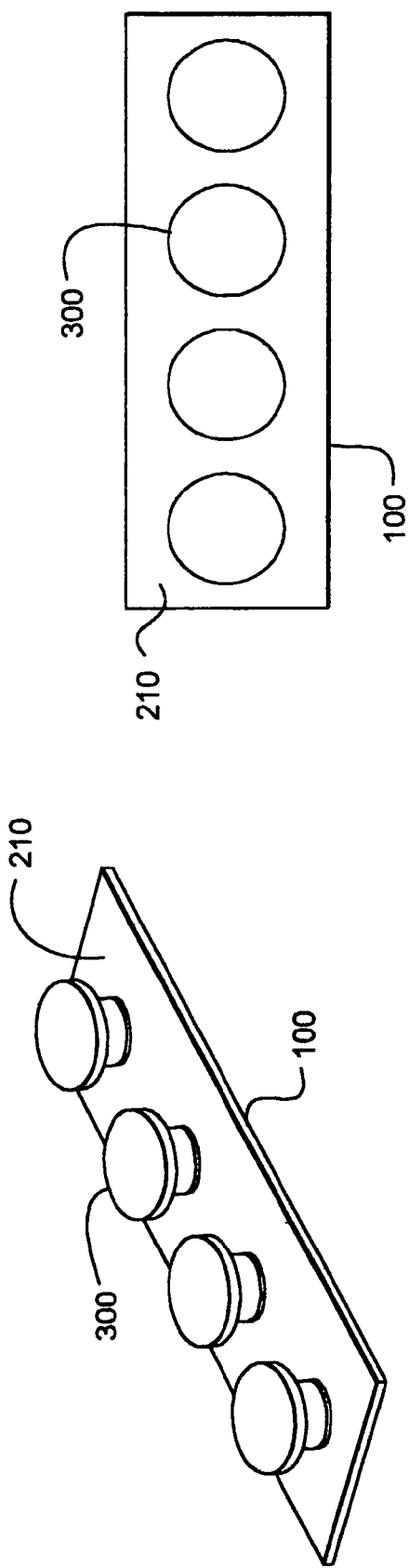
FIG. 6A
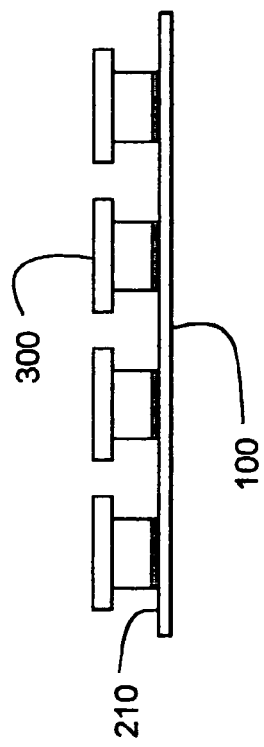
FIG. 6B
FIG. 6C

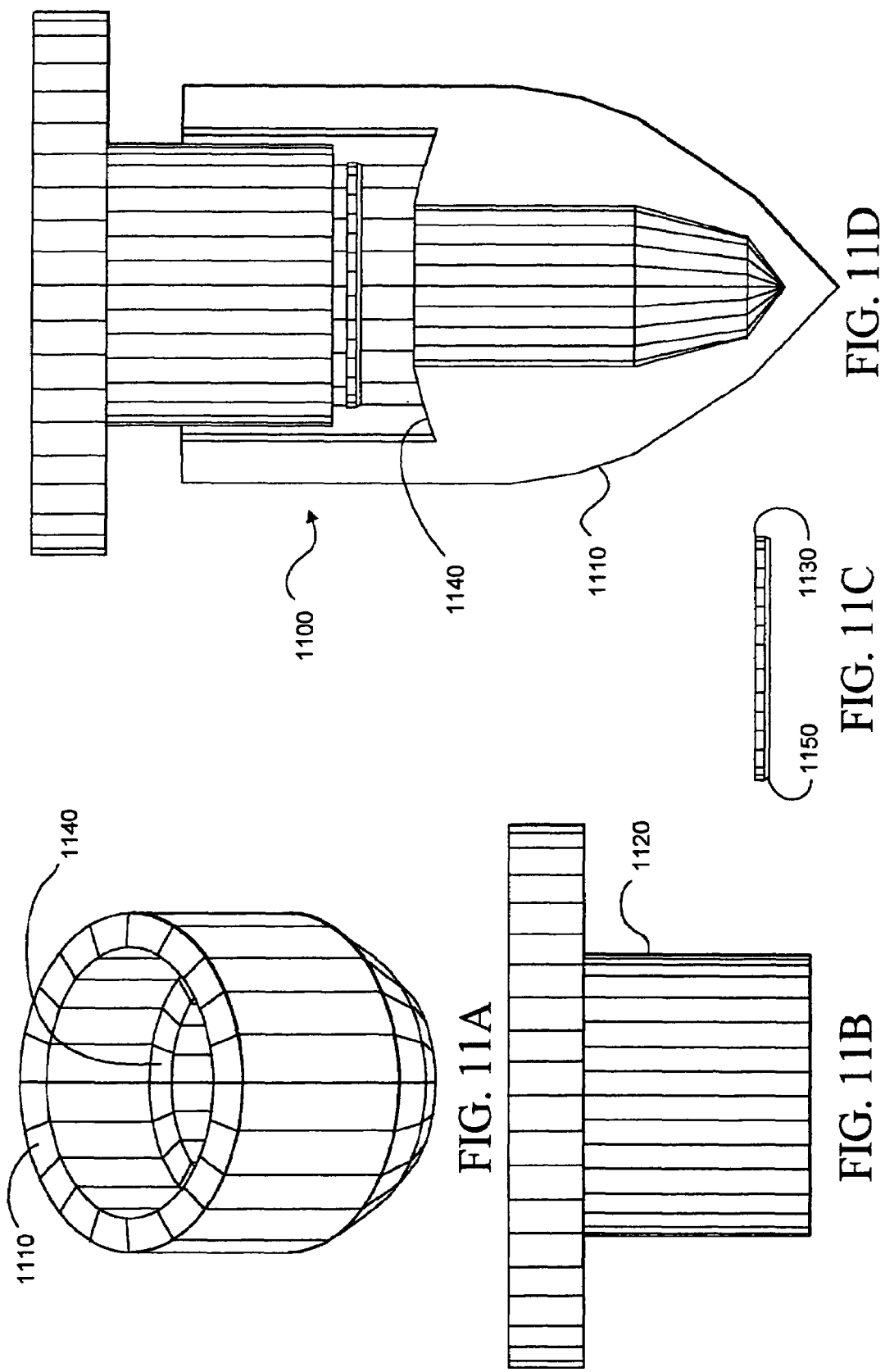

CONSUMABLE FOR LASER CAPTURE MICRODISSECTION

CROSS-REFERENCE TO RELATED APPLICATION

This application is a continuation-in-part under 35 U.S.C. 120 of U.S. Ser. No. 60/060,732, filed Oct. 1, 1997, now pending, the entire contents of which are hereby incorporated by reference as if fully set forth herein.

BACKGROUND OF THE INVENTION

1. Field of the Invention

The present invention relates generally to the field of laser capture microdissection (LCM). More particularly, the present invention relates to apparatus for acquiring LCM samples that include an LCM film mounted on at least a part of the interior of an analysis container. Specifically, a preferred implementation of the present invention relates to a substantially planarized ethylene vinyl acetate (EVA) polymer LCM film that is hot vacuum baked onto the bottom of a microcentrifuge tube cap. The present invention thus relates to an LCM sample acquisition apparatus of the type that can be termed planar cap.

2. Discussion of the Related Art

Diseases such as cancer have long been identified by examining tissue biopsies to identify unusual cells. The problem has been that there has been no satisfactory prior-art method to extract the cells of interest from the surrounding tissue. Currently, investigators must attempt to manually extract, or microdissect, cells of interest either by attempting to mechanically isolate them with a manual tool or through a convoluted process of isolating and culturing the cells. Most investigators consider both approaches to be tedious, timeconsuming, and inefficient.

A new technique has been developed which can extract a small cluster of cells from a tissue sample in a matter of seconds. The technique is called laser capture microdissection (LCM). Laser capture microdissection is a one-step technique which integrates a standard laboratory microscope with a low-energy laser and a transparent ethylene vinyl acetate polymer thermoplastic film such as is used for the plastic seal in food product packaging.

In laser capture microdissection, the operator looks through a microscope at a tissue biopsy section mounted on a standard glass histopathology slide, which typically contains groups of different types of cells. A thermoplastic film is placed over and in contact with the tissue biopsy section. Upon identifying a group of cells of interest within the tissue section, the operator centers them in a target area of the microscope field and then generates a pulse from a laser such as a carbon dioxide laser having an intensity of about 50 milliwatts (mW) and a pulse duration of between about 50 to about 500 milliseconds (mS). The laser pulse causes localized heating of the plastic film as it passes through it, imparting to it an adhesive property. The cells then stick to the localized adhesive area of the plastic tape directly above them, whereupon the cells are immediately extracted and ready for analysis. Because of the small diameter of the laser beam, extremely small cell clusters may be microdissected from a tissue section.

By taking only these target cells directly from the tissue sample, scientists can immediately analyze the gene and enzyme activity of the target cells using other research tools. Such procedures as polymerase chain reaction amplification of DNA and RNA, and enzyme recovery from the tissue sample have been demonstrated. No limitations have been reported in the ability to amplify DNA or RNA from tumor cells extracted with laser capture microdissection.

Laser capture microdissection has successfully extracted cells in all tissues in which it has been tested. These include kidney glomeruli, in situ breast carcinoma, atypical ductal hyperplasia of the breast, prostatic interepithielial neoplasia, and lymphoid follicles. The direct access to cells provided by laser capture microdissection will likely lead to a revolution in the understanding of the molecular basis of cancer and other diseases, helping to lay the groundwork for earlier and more precise disease detection.

Another likely role for the technique is in recording the patterns of gene expression in various cell types, an emerging issue in medical research. For instance, the National Cancer Institute's Cancer Genome Anatomy Project (CGAP) is attempting to define the patterns of gene expression in normal, precancerous, and malignant cells. In projects such as CGAP, laser capture microdissection is a valuable tool for procuring pure cell samples from tissue samples.

The LCM technique is generally described in the recently published article: Laser Capture Microdissection, *Science*, Volume 274, Number 5289, Issue 8, pp 998–1001, published in 1996, the entire contents of which are incorporated herein by reference. The purpose of the LCM technique is to provide a simple method for the procurement of selected human cells from a heterogeneous population contained on a typical histopathology biopsy slide.

A typical tissue biopsy sample consists of a 5 to 10 micron slice of tissue that is placed on a glass microscope slide using techniques well known in the field of pathology. This tissue slice is a cross section of the body organ that is being studied. The tissue consists of a variety of different types of cells. Often a pathologist desires to remove only a small portion of the tissue for further analysis.

LCM employs a thermoplastic transfer film that is placed on top of the tissue sample. This film is manufactured containing organic dyes that are chosen to selectively absorb in the near infrared region of the spectrum overlapping the emission region of common AlGaAs laser diodes. When the film is exposed to the focused laser beam the exposed region is heated by the laser and melts, adhering to the tissue in the region that was exposed. The film is then lifted from the tissue and the selected portion of the tissue is removed with the film.

Thermoplastic transfer films such as a 100 micron thick ethyl vinyl acetate (EVA) film available from Electroseal Corporation of Pompton Lakes, N.J. (type E540) have been used in LCM applications. The film is chosen to have a low melting point of about 90° C.

The thermoplastic EVA films used in LCM techniques have been doped with dyes, such as an infrared napthalocyanine dye, available from Aldrich Chemical Company (dye number 43296-2 or 39317-7). These dyes have a strong absorption in the 800 nm region, a wavelength region that overlaps with laser emitters used to selectively melt the film. The dye is mixed with the melted bulk plastic at an elevated temperature. The dyed plastic is then manufactured into a film using standard film manufacturing techniques. The dye concentration in the plastic is about 0.001 M.

While the films employed in LCM applications have proved satisfactory for the task, they have several drawbacks. The optical absorption of a dye impregnated film is a function of its thickness. This property of the film may be in conflict with a desire to select film thickness for other reasons.

The organic dyes which are used to alter the absorption characteristics of the films may have detrimental photochemistry effects in some cases. This could result in contamination of LCM samples. In addition, the organic dyes employed to date are sensitive to the wavelength of the incident laser light and thus the film must be matched to the laser employed.

SUMMARY OF THE INVENTION

An object of the invention is to improve the speed of the laser capture microdissection technique. Another object of the invention is to improve the accuracy of the laser capture microdissection technique. Another object of the invention is to improve the reproducibility of the laser capture microdissection technique. Yet another object of the invention is to reduce the amount of contamination involved with the laser capture microdissection technique. Therefore, there is a particular need for an LCM consumable that integrates an LCM film into the interior of an analysis container. A planar cap includes a substantially planarized ethylene vinyl acetate (EVA) polymer LCM film that is hot vacuum baked onto the bottom of a microcentrifuge tube cap. The laser capture microdissection caps can be shipped as-baked (i.e., packaged without post-bake processing) to protect the laser capture microdissection transfer film and minimize contamination. The cap, and the configuration in which it is shipped, provides the additional advantages of quick and easy utilization. Thus, it is rendered possible to simultaneously satisfy the requirements of speed, accuracy and resistance to contamination, which, in the case of the prior art, are mutually contradicting and cannot be simultaneously satisfied.

A first aspect of the invention includes a laser capture microdissection assembly comprising: a plate having a substantially planar top surface; and at least one laser capture microdissection cap connected to said substantially planar top surface of said plate, wherein said at least one laser capture microdissection cap includes a transfer film carrier having a substrate surface; and a substantially planarized laser capture microdissection transfer film connected to said substrate surface of said transfer film carrier. A second aspect of the invention includes a laser capture microdissection apparatus, comprising: a transfer film carrier having a substrate surface; and a laser capture microdissection transfer film coupled to said substrate surface of said transfer film carrier, said laser capture microdissection transfer film including at least one integrally formed structural feature that protrudes and provides a controllable spacing between said laser capture microdissection transfer film and a sample. A third aspect of the invention includes an integral portion of a biological reaction vessel, comprising: a transfer film carrier having a substrate surface; and a laser capture microdissection transfer film coupled to said substrate surface of said transfer film carrier. A fourth aspect of the invention includes a laser capture microdissection assembly comprising: a plate having a top surface; and at least one laser capture microdissection cap coupled to said top surface of said plate, wherein each of said at least one laser capture microdissection cap includes a transfer film carrier having a substrate surface; and a laser capture microdissection transfer film coupled to said substrate surface of said transfer film carrier.

A fifth aspect of the invention includes a method of making the laser capture microdissection assembly comprising: providing a plate having a substantially planar top surface; providing at least one laser capture microdissection cap, said at least one laser capture microdissection cap including a transfer film carrier having a substrate surface; providing a laser capture microdissection transfer film adjacent to said substrate surface of said transfer film carrier; and hot vacuum baking said at least one laser capture microdissection cap and said plate so as to substantially planarize said laser capture microdissection transfer film. A sixth aspect of the invention includes a method of making a laser capture microdissection consumable, comprising: providing a transfer film carrier having a substrate surface; and forming a laser capture microdissection transfer film on said substrate surface, wherein forming includes hot vacuum baking said laser capture microdissection transfer film. A seventh aspect of the invention includes a method of making an integral portion of a biological reaction vessel, comprising: providing a transfer film carrier having a substrate surface; and fabricating a laser capture microdissection transfer film on said substrate surface. An eight aspect of the invention includes a method of making a laser capture microdissection assembly, comprising: providing a plate having a top surface; providing at least one laser capture microdissection cap, said at least one laser capture microdissection cap including a transfer film carrier having a substrate surface; providing, for said at least one laser capture microdissection cap, a laser capture microdissection transfer film coupled to said substrate surface of said transfer film carrier; placing said at least one laser capture microdissection cap in contact with said plate; and hot vacuum baking both said at least one laser capture microdissection cap and said plate so as to produce said laser capture microdissection assembly.

A ninth aspect of the invention includes a method of imaging a sample with a microscope, comprising: providing said microscope; locating a scattering media within a beam path defined by said microscope and within a few millimeters of a sample; and imaging said sample through said scattering media with said microscope. A tenth aspect of the invention includes a microscope, comprising: a scattering media located within a beam path defined by said microscope and within a few millimeters of a sample.

These, and other, aspects of the present invention will be better appreciated and understood when considered in conjunction with the following description and the accompanying drawings. It should be understood, however, that the following description, while indicating preferred embodiments of the present invention and numerous specific details thereof, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the components and operation of model systems provided with the present invention, will become more readily apparent by referring to the exemplary, and therefore nonlimiting, embodiments illustrated in the drawings accompanying and forming a part of this specification, wherein like reference numerals (if they occur in more than one view) designate the same elements. Consequently, the claims are to be given the broadest interpretation that is consistent with the specification and the drawings. It should be noted that the features illustrated in the drawings are not necessarily drawn to scale.

FIGS. 5A–5C illustrate three views of an assembly that includes four of the sample carriers depicted in FIGS. 4A–4D and one of the plates depicted in FIGS. 2A–2C, representing an embodiment of the present invention;

FIGS. 6A–6C illustrate three views of a completed assembly after vacuum hot cast molding, representing an embodiment of the present invention;

FIGS. 11A–11D illustrates a several views of a biological reaction vessel, representing an embodiment of the invention.

DESCRIPTION OF PREFERRED EMBODIMENTS

The present invention and the various features and advantageous details thereof are explained more fully with reference to the nonlimiting embodiments that are illustrated in the accompanying drawings and detailed in the following description. Descriptions of well known components and processing techniques are omitted so as not to unnecessarily obscure the present invention in detail.

The entire contents of U.S. Ser. No. 60/037,864, filed Feb. 7, 1997; U.S. Ser. No. 08/797,026, filed Feb. 7, 1997; U.S. Ser. No. 08/800,882, filed Feb. 14, 1997; U.S. Ser. No. 60/060,731, filed Oct. 1, 1997; and U.S. Ser. No. 60/060,732, filed Oct. 1, 1997 are hereby expressly incorporated by reference into the present application as if fully set forth herein.

Figure 1A:
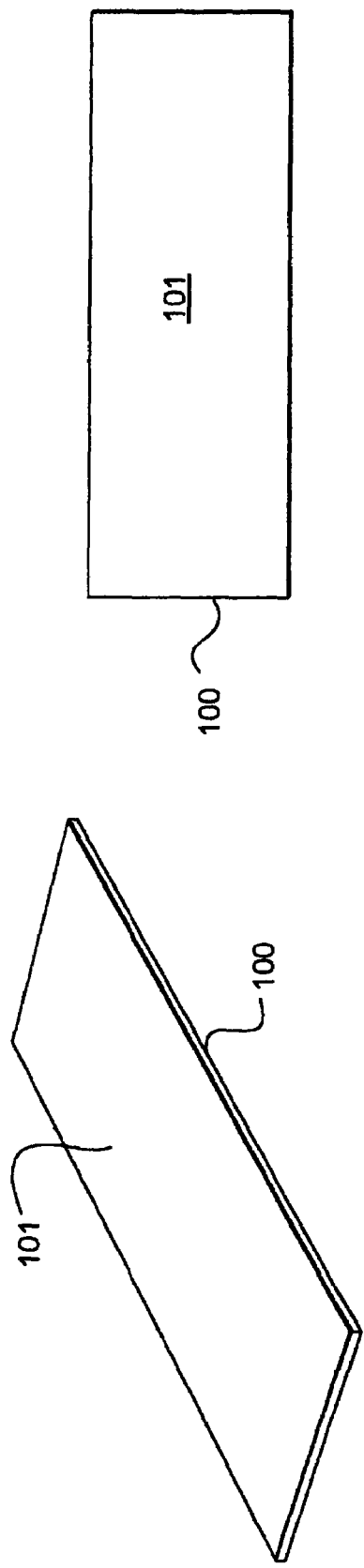
FIGS. 1A–1C illustrate three views of a laser capture microdissection (LCM) sample plate, representing an embodiment of the present invention.
Figure 1B:
Figure 1C:
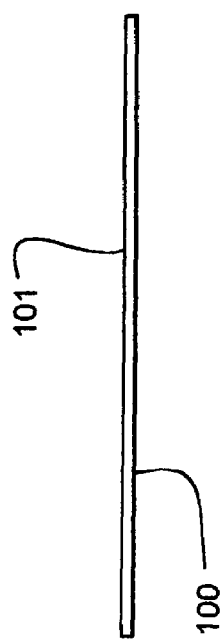

Turning to FIGS. 1A–1C, a plate 100 is depicted. Plate 100 can be fabricated from metal, glass, ceramic, or any other material suitable for the subsequent processing steps described below. In a preferred embodiment, plate 100 is a glass microscope slide. It is important that the top surface 101 of plate 100 be flat. Although the depicted embodiment shows a bare microscope slide, the plate can be coated, or otherwise surface treated, in a preliminary processing step.

Figure 2B:
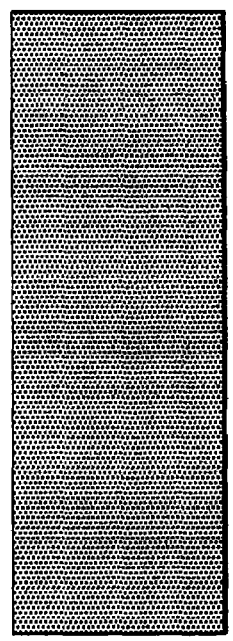
FIGS. 2A–2C illustrate three views of the sample plate shown in FIGS. 1A–1C after coating with a release agent, representing an embodiment of the present invention.
Figure 2A:
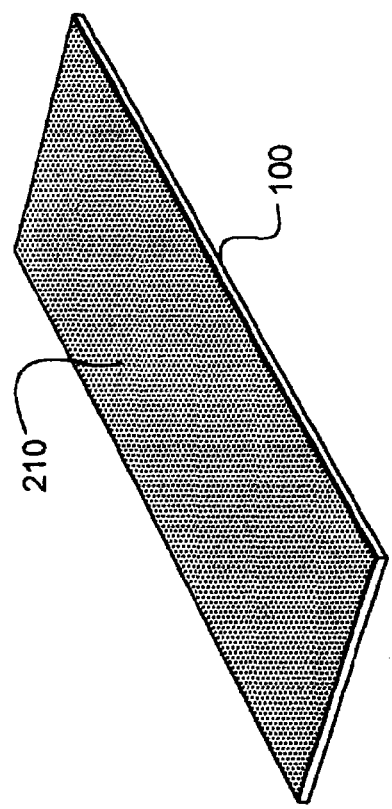
Figure 2C:
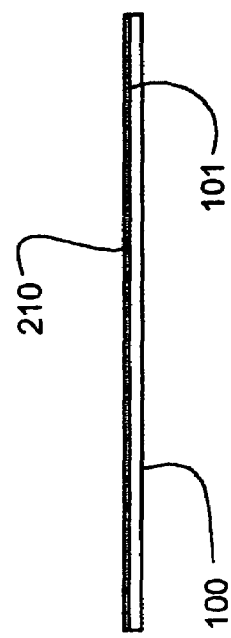
Figure 3C:
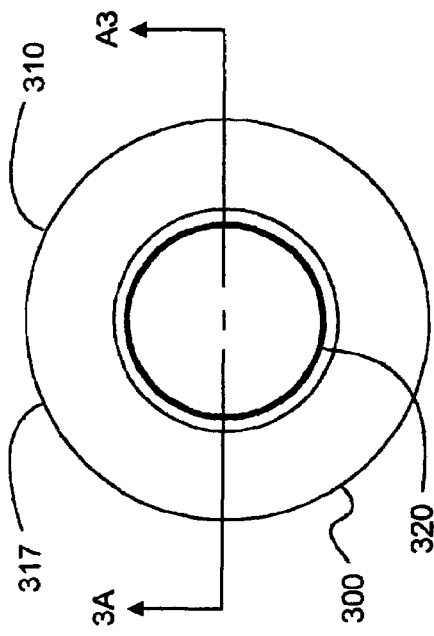
FIGS. 3A–3D illustrate four views of a sample carrier, representing an embodiment of the present invention.
Figure 3D:
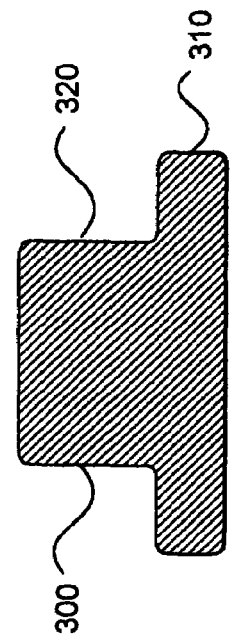
Figure 3A:
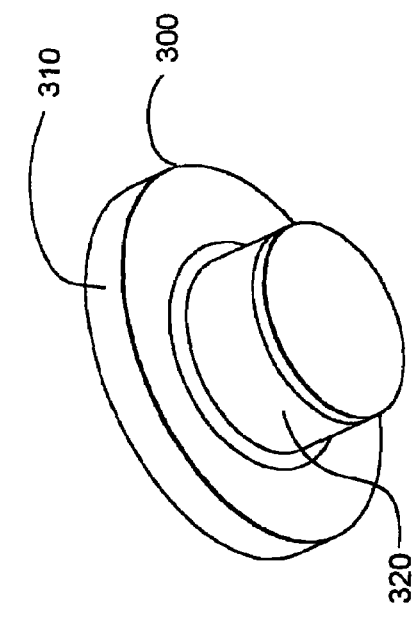
Figure 3B:
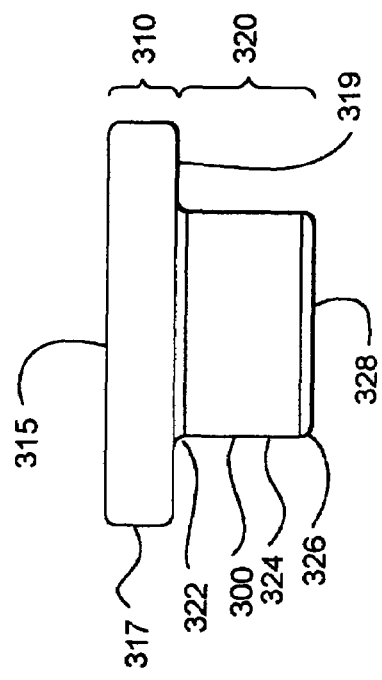
Figure 4C:
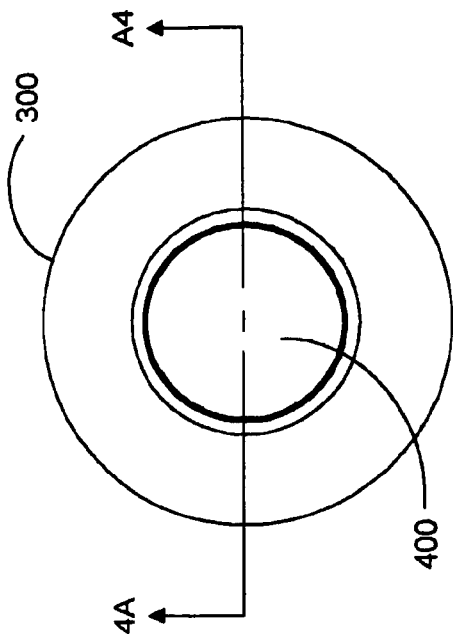
FIGS. 4A–4D illustrate four views of the sample carrier illustrated in FIGS. 3A–3D after an LCM film is added, representing an embodiment of the present invention.
Figure 4D:
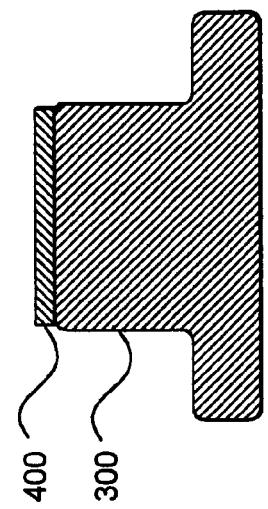
Figure 4A:
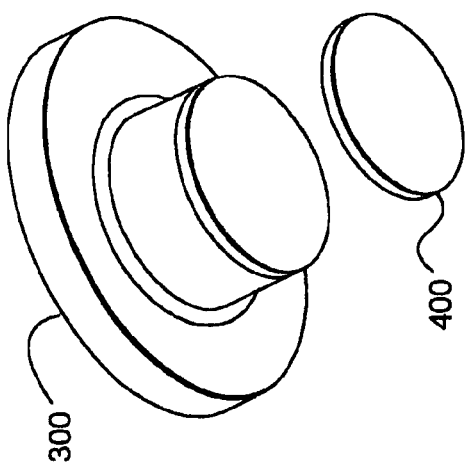
Figure 4B:
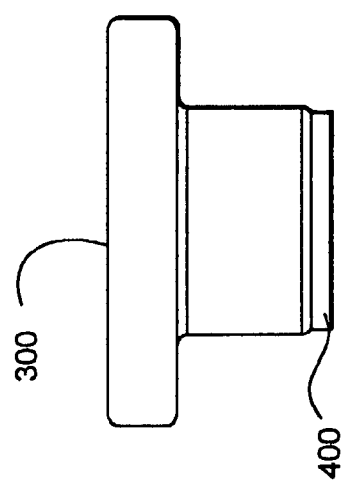

Turning now to FIGS. 2A–2C, the plate 100 is depicted with a release agent 210. The release agent 210 is applied to the top surface 101. It will be noted that the top surface 101 is obscured by the release agent 210 in FIGS. 2A–2B but is clearly visible as an interface in FIG. 2C.

The release agent can be any suitable nonadhesive material such as, for example, silicones, or TEFLON (i.e., polytetrafluoroethylene). Advantageously, the release coating can be a surfactant that increases the contact angle of liquids with which it comes in contact. It is important that the release agent 210 maintain and extend the flatness provided initially by the top surface 101. In a preferred embodiment, the release agent 210 can include a silicone containing surfactant agent such as, for example, RAIN-X.

Turning now to FIGS. 3A–3D, a sample carrier 300 is depicted. The sample carrier 300 has an upper portion 310 and a lower portion 320. The upper portion 310 includes a top surface 315 and an outer perimeter 317, and a shoulder 319. The lower portion 320 includes a flare 322, an inner perimeter 324, a taper 326 and a substrate surface 328.

The sample carrier 300 can be a polymeric cap that is of transparent optical quality. For example, the cap could be fabricated from polycarbonate, or other suitable optically transparent plastic. However, the cap does not need to be optically transparent provided the absorption characteristics of the polymer from which it is made are compatible with suitable transmission of the laser energy to the capture film.

Turning now to FIGS. 4A–4D, a laser capture microdissection (LCM) transfer film 400 is shown being applied to the sample carrier 300. It will be appreciated that the LCM transfer film 400 is depicted out of scale for the sake of clarity. The laser capture microdissection transfer film 400 can be applied to the bottom of a circular cap by punching a circular section from a free-standing sheet of ethylene vinyl acetate. Alternatively, the LCM transfer film 400 can be molded to the bottom of the cap. The LCM transfer film 400 can be deposited on the cap using a process such as spin coating, dipping, or spraying. In any event, manufacture of the consumable should be carried out in a sterile environment.

It is advantageous that the LCM transfer film 400 be thin. For example, a 50 micron thick film is preferable to a 100 micron thick film. However, the film can advantageously be fabricated in thicknesses of approximately 500, 400, 300, 200, 100, 50 microns, or less.

Turning to FIGS. 5A–5C, a plurality of combined sample carriers 300 together with their corresponding LCM transfer films 400 are depicted being lowered toward the release agent 210 that is coated on top of the plate 100. The LCM transfer films 400 can be an ethylene vinyl acetate (EVA) polymeric material. It will appreciated that FIG. 5A depicts the assembly process at an earlier point in time compared to FIG. 5C wherein the gap between the LCM transfer film 400 and the release agent 210 is almost closed.

Turning now to FIGS. 6A–6C, the assembly of four sample carriers 300 on plate 100 is depicted during the process step of vacuum hot baking. The process of vacuum hot baking causes the EVA to soften, melt and flow thereby conforming to the substantially planar surface presented by the release agent 210. In this way, the flatness possessed by the plate 100 is transferred to the LCM transfer film 400. This also eliminates trapped air.

The hot vacuum baking of the film can take place in moderate vacuum. In a preferred embodiment, the hot cast molding takes place at one torr and 95 degrees C. for approximately one hour.

In an alternative embodiment, instead of attaching the LCM film to the base of the cap prior to its placement on top of the release agent coated plate, the LCM film can be coated on top of the release agent as a film layer. A sample carrier can then be placed on top of the LCM film. An assembly of one, or more, such combinations can then be subjected to hot vacuum melt casting to planarize at least that portion of the LCM film that is located at the interface between the sample carrier and the release agent. In this way, when the sample carrier is removed from the plate, a portion of the planarized LCM film that corresponds with the bottom surface of the sample carrier will be broken away from the assembly together with the cap that is being removed. Those portions of the LCM film that are not adjacent the bottom of the cap being removed will remain on the plate. In a preferred embodiment, when the sample carrier is pulled away from the plate, a twisting motion is applied to the sample carrier either before and/or during linear separation of the two prime components so as to exert a sheer force both within the LCM film and between the LCM film and the release layer.

The release coating can be a silicone. Alternatively, the release coating can be a polytetrafluoroethylene.

Throughout this specification, the more descriptive phrase "transfer film carrier" can be substituted for the phrase "sample carrier." In general, the transfer film carrier carries the transfer film. Only that portion of the sample that is transferred to the transfer film is carried by the carrier.

The ethylene vinyl acetate can be selected from among the available materials based on the following criteria. The ethylene vinyl acetate should have a high melt index. A high melt index is indicated by low viscosity and low molecular weight.

It is important that the ethylene vinyl acetate, or other material being used for the LCM transfer film, have a modest tack. Thus, the transfer film is somewhat sticky but will not bind to everything with which it comes in contact.

The caps can be made from clear plexiglass G (i.e., polymethyl methacrylate). By treating the glass slide with a surfactant before the caps are vacuum hot cast in place, the completed caps can be popped off the glass slide just before they are needed for acquisition of sample material.

In a preferred embodiment, the cap is sized to fit in a standard microcentrifuge tube. The LCM transfer film can be attached to the cap using glue, or by welding the thermoplastic, or by some other mechanical means, holding the film in place.

The side walls of the cap can have a negative draft. This negative draft can be machined into the tooling with which the caps are made.

After capturing the tissue to be analyzed on the bottom of the cap, the cap is placed on the microcentrifuge tube containing proteinase (i.e., protease, e.g., Trypsin) solution and the tube is inverted. The tissue is then dissolved and the DNA is free to enter the solution. The solution is then pipetted out of the tube and into the PCR mixture.

While not being bound by theory, it is believed that the EVA film expands both up and down when it is exposed to the energy from the laser. As an approximation, it is believed that the EVA film expands approximately 12–15% downward and upward when it is exposed to the LCM charge from the laser. The upward expansion is restricted by the plastic cap.

The thickness of the LCM transfer film should be held to within 20%, preferably 5%. The bottom, exposed surface of the LCM transfer film can be termed a capture surface. The flatness of the LCM transfer film should be held to within approximately five microns, preferably approximately one micron. The flatness of the film can readily characterized based on the number of fringes multiplied by $\lambda/2$. The flatness of the LCM transfer film should preferably be held to within two waves which is approximately equal to ¼ micron per fringe, given a $\lambda$ of 540 nm.

The dye in the ethylene vinyl acetate is what absorbs the laser energy. The ethylene vinyl acetate transforms to a liquid phase, infuses into the cell structure of interest and then hardens.

The particular manufacturing process used for fabricating the assembly should be inexpensive and reproducible. Conveniently, the fabrication of the present invention can be carried out by using any coating and baking method. It is preferred that the process be conducted in a contaminant-free environment. For the manufacturing operation, it is moreover an advantage to employ an automated method.

However, the particular manufacturing process used for fabricating the assembly is not essential to the present invention as long as it provides the described assembly. Normally those who make or use the invention will select the manufacturing process based upon tooling and energy requirements, the expected application requirements of the final product, and the demands of the overall manufacturing process.

The particular material used for the cap should be biologically and chemically inert. Conveniently, the cap of the present invention can be made of any material with a melting point higher than that of EVA. It is preferred that the material be inexpensive. For the manufacturing operation, it is moreover an advantage to employ a transparent thermoplastic material that can be injection molded or machined. For example, the cap can include polymethyl methacrylate. By proper selection of the polymeric materials, the cap can be solid. There is no need for a through-hole through the center axis of the cap.

However, the particular material selected for the cap is not essential to the present invention, as long as it provides the described function. Normally, those who make or use the invention will select the best commercially available material based upon the economics of cost and availability, the expected application requirements of the final product, and the demands of the overall manufacturing process.

The LCM transfer film can be any suitable thermoplastic. For example, the LCM transfer film can include one or more of: EVAs; polyurethanes (PU); polyvinyl acetates; ethylene-methyl acrylate (EMAC); polycarbonate (PC); ethylene-vinyl alcohol copolymers (EVOH); polypropylene (PP); and expandable or general purpose polystyrene (PS). ELVAX 410, 200 and 205 are suitable resins of EVA that are commercially available from DuPont wherein the operative variant is the amount of vinyl.

The LCM transfer film can include an absorptive substance. The absorptive substance can include an absorptive dye. This dye can be either a broad band absorptive dye or a frequency specific absorptive dye. For example, the absorptive dyes can include one or more of: tin(IV) 2,3-naphthalocyanine dichloride; silicon(IV) 2,3-naphthalocyanine dihydroxide; silicon (IV) 2,3-naphthalocyanine dioctyloxide; and vanadyl 2,11,20,29-tetra-tert-butyl-2,3-naphthalocyanine. Also, the absorptive substance can include a plurality of Fullerines (i.e., Bucky Balls, e.g., C60).

The LCM transfer film can also include a scattering media. Since the LCM transfer film is very close to the sample, the scattering media reduces shadows, thereby improving the process of imaging. The scattering media can include a diffusing material. For example, the LCM transfer film can be loaded with a small particulate material that scatters the illumination light so as to minimize shadows and improve imaging without detrimentally effecting the LCM beam. Alternatively, the transfer film can include a dichromatic gelatin (DCG) to perform the same functions. The DCG can be exposed and developed to provide specific diffuser properties within the transfer film such as shaping.

There are a variety of techniques for building a noncontact LCM transfer film and/or carrier. The purpose of the noncontact LCM approach is to provide a method for the elimination of problems associated with nonspecific binding of tissue to an LCM film. In more detail, if a sample slide has areas with loosely attached cells, these portions of the sample can be lifted mistakenly from the slide due to nonspecific attachment to the LCM film. That is, these areas stick to the film even though they were not illuminated by the laser. If these portions are transferred to the reagent vessel they will be digested by the reagents and appear as contaminants in the sample. It is important to prevent the loosely bound tissue areas from contacting the film.

One method for preventing the contact of the film to areas of tissue that might nonspecifically transfer is to offset (distance) the film a few microns from the tissue sample. In the area illuminated by the laser, the film expands roughly 10% of its thickness (about 5 to 10 microns based on a typical thickness of 50 to 100 microns) and contacts the tissue, thereby allowing transfer in the illuminated region. Outside this region, the film and tissue never come in contact because the film is spaced away from the tissue. The film, however, must not be spaced too far from the tissue (greater than a few microns) since the film needs to contact the tissue after its expands due to the laser illumination.

One technique to make a noncontact LCM transfer film that "stands-off" a few microns is to create a series of pedestals that are a few microns high so as to provide a series of standoffs for the cap to rest on. These pedestals can be created by exposing edges of the transfer film to the focused laser beam. The laser beam distorts the normally flat film in the focal region raising the surface in this region. By placing these pedestals at the vertices of an equilateral triangle with points located at the rim of the transfer film carrier a good three-point mount is provided. The height of these pedestals can be adjusted by changing the power and pulse length of the focused laser beam. The diameter can be adjusted by changing the diameter of the laser beam. The exposure levels are similar to the levels used for tissue transfer: approximately 10–90 mW for approximately 10–90 milliseconds. (To create the pedestals it may help to expose the film when it is in contact with a glass slide.) The reagent vial can be constructed so that it has an internal rim that contacts the pedestals, sealing them from the reagent, thereby preventing tissue that might be on the pedestals from contaminating the sample.

Figure 7A:
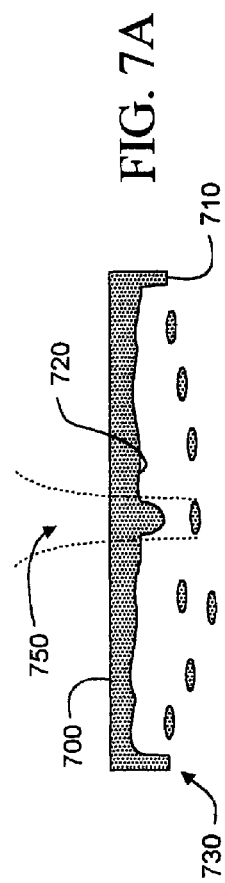
FIGS. 7A–7B illustrate two sequential views of a laser capture microdissection film with molded features, representing an embodiment of the present invention.
Figure 7B:
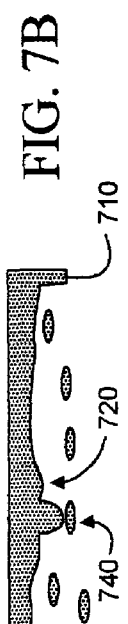

Turning now to FIGS. 7A–7B, an LCM film 700 can be provided with features 710. The features 710 can include a raised portion 720 (pedestal) and a protruding feature 730 (e.g., rim). The features 710 can be molded (e.g., replicated), or otherwise formed (e.g., by laser), in the LCM film 700. Such features give the LCM film 700 a working surface that defines a topography.

The purpose of the features 710 is to provide an additional way of selecting single cells from a tissue sample using LCM, other than just a very small laser spot size. The features 710 that are fabricated into the LCM transfer film can be roughly the size of a desired cell 740. The features 710 can extend out from the film surface for a distance of several microns.

The film 700 itself can be offset from the cells a distance of from approximately 5 to approximately 10 microns by the protruding feature 730 that runs around the circumference of the cap. To stabilize the plane of the film, it will be appreciated that the protruding feature only needs to extend along at least three points of a perimeter of the film and does not need to be a continuous rim.

The features 710 can be fabricated by hot cast molding the LCM film 700 against a mold that has complimentary shapes of the features laser machined into the mold surface. Such a mold can be made out of a polished metal surface or a glass surface using a Q-switched laser focused to a diameter of from approximately 5 to approximately 20 microns. The features 710 can also be fabricated by molding the film against a mold surface that is micromachined with a diamond stylus. The topography is transferred from the mold to the film via replication.

A protuberance (raised portion 720) for acquiring the desired cell 740 can include a small raised area of LCM film roughly 5 to 20 microns in diameter. When a laser beam 750 heats this portion of the film, the raised portion 720 will contact the tissue first and the laser power can be adjusted so that the surrounding adjacent film regions do not contact the tissue. Thus, the raised portion 720 provides spatial discrimination in addition to the spatial discrimination provided by the position, size and mode of the laser beam. An advantage of the features 710 is that a larger laser beam could be used and a researcher or laboratory technician could still achieve single cell lift-off. The raised portion of the film (raised portion 720) will be heated to a higher temperature than the surrounding flat film area. The protruding feature 730 (i.e., the rim) will not be heated. This would also increase the likelihood that a cell in the region of the feature would be captured exclusively. Of course, it is advantageous that raised portion 720 not protrude as far as protruding feature 730.

Figure 8:
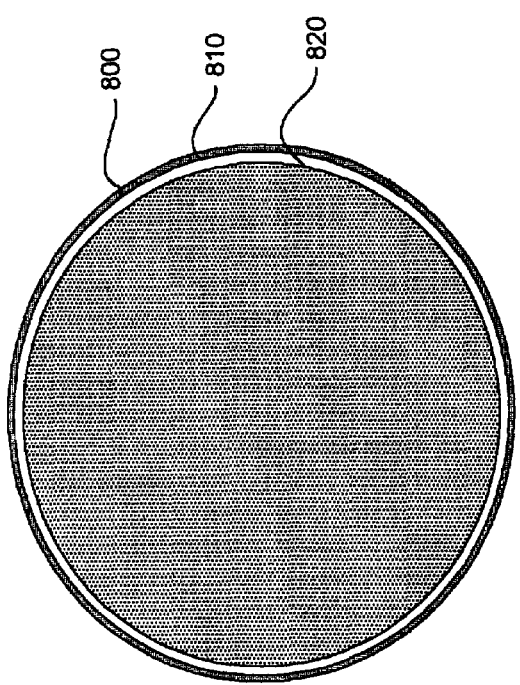
FIG. 8 illustrates a bottom view of a laser capture microdissection film with molded features, representing an embodiment of the present invention.

Referring now to FIG. 8, multiple pedestals 800 could be molded into an LCM film 810 to allow multiple single cell lift off regions. The LCM film 810 could again include a rim 820. Multiple cells could then be analyzed in a single microcentrifuge tube.

The structural feature (i.e., spacer) that holds the film away from the sample can be hot vacuum baked into the transfer film. According to this process, a negative of the structural feature can be formed in a plate. The structural feature is then replicated (as a positive) in the film when it is heated and flows into the void defined by the negative of the feature. Alternatively, the structural feature can be formed in the transfer film with the use of a laser, or even with micro-machining equipment.

The structural feature, or spacer, can be integrally formed in the laser capture microdissection transfer film. The structural feature provides a separation between the transfer film and the sample. This separation holds the film away from the sample, thereby enabling noncontact laser capture microdissection.

The transfer film can be connected to the substrate surface with a refractive index matching transparent fluid or glue. Alternatively, the transfer film can be coupled to the substrate surface by punching both the sample carrier and the transfer film from stock material simultaneously. It is even possible to couple the film to the carrier with double-sided tape.

The laser capture microdissection transfer film includes a substantially planarized low land area. This low land area can be provided with structural features that protrude so as to define a laser capture microdissection acquisition zone. These protrusions can be termed pedestals. The low land can also be provided with structural features that hold most of the film away from the sample. In order to support the plane of the film, it is preferable to have at least three such supporting features. If these supporting features run around most, or all, of a perimeter of a transfer film, they can be termed a rim.

Whatever contacts the tissue needs to be equidistant from the tissue so that the dosimetry is constant across the transfer film. In this way, a known distance between the tissue and the transfer film can be established. In many cases such a known distance will be fixed across substantial portions of the transfer film surface. However, it is sufficient that the distance be known and does not need to be fixed. The distance needs to be known for the purpose of adjusting laser power so as to achieve tissue transfer.

When the transfer film is exposed to the electromagnetic energy, it expands (both up and down) against the substrate surface and contacts the tissue, thereby injecting itself into the sample. In the case where there is a space between the transfer film and the top surface of the sample, (noncontact laser capture microdissection) the expanding film will be projected through that space before it contacts the top surface of the sample at the beginning of the injection phase.

Figures 9, 10:
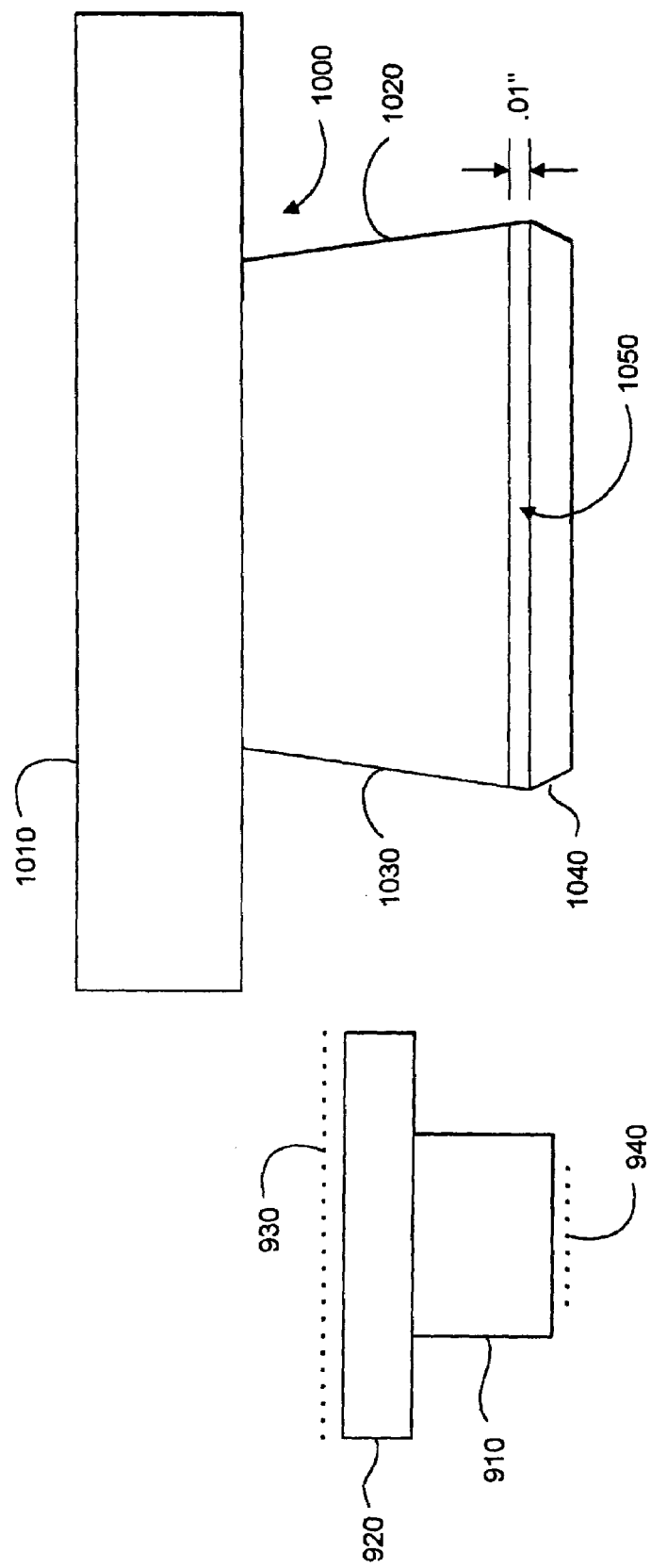
FIG. 9 illustrates a side view of a laser capture microdissection apparatus, representing an embodiment of the invention.
FIG. 10 illustrates a side view of a microcentrifuge tube cap with a negative draft, representing an embodiment of the invention.

Referring now to FIG. 9, a scatter illuminator design for an LCM device is illustrated. The purpose of the scatter illuminator design is to provide a more appropriate illuminator for an LCM microscope that generates a more even illumination to prevent shadows from obscuring internal cell structure.

A laser capture microdissection apparatus includes a top portion 910 and a bottom portion 920. The top portion 910 includes an upper surface to which a scattering media 930 can be coupled. The bottom portion 920 includes a substrate surface to which a scattering media 940 can be coupled. Either, or both, of the scattering media 930 and 940 can be used. The scattering media can be incorporated into the transfer film carrier and/or the LCM transfer film.

Using a standard inverted microscope light source and placing a scattering media (e.g., a piece of paper) near the tissue to scatter the light results in dramatically improved illumination of the sample and much better visualization. A scattering media of this type eliminates the need for refractive index matching of the sample. Such a scattering media can allow visualization of the cell nucleus and other subcellular structures that would normally be obscured by normal illumination techniques.

The scattering media can be a diffuser material. A diffuser material that is suitable for use as the scattering media is milk glass which is a very dense, fine diffuser available from Edmund Scientific as Part No. P43,717. Standard laser printer/photocopier paper can even be used as the scattering media. Other types of transparent scattering media can be used, such as, for example, frosted glass, a lenticular sheet, a volume diffuser, and/or a surface diffuser. In any event, the scattering media should be a material that aggressively scatters the illumination light. A single sheet of typical ground glass is generally inadequate and needs to be combined in multiple layers as a serial stack of three or four sheets of ground glass to diffuse the illumination light sufficiently.

The scattering media can be directly or indirectly connected to the transfer film carrier and/or the LCM transfer film. Alternatively, the scattering media can be formed on a surface of, or the interior of, the transfer film carrier and/or the LCM transfer film. The scattering media can be fabricated so as to shape the LCM beam and/or the illumination beam. The scattering media needs to be within a few millimeters of the sample to be effective. A few millimeters means less than one centimeter, preferably less than five millimeters.

Referring now to FIG. 10, a laser capture microdissection apparatus 1000 is illustrated. The apparatus 1000 includes a top portion 1010 and a bottom portion 1020. The bottom portion 1020 includes a negative draft 1030. The negative draft 1030 is preferably approximately 5°. The bottom portion 1020 also includes a chamfer 1040. The chamfer 1040 is preferably approximately 20°. The bottom portion 1020 also includes a girdle 1050. The width of the girdle 1050 for line contact with the interior of an analysis vessel is preferably approximately 0.01". Caps with a negative draft can be fabricated with a break-apart plastic injection molding die. Alternatively, negative draft caps can be fabricated by interpolation with computer numeric control cutting tool machinery.

Turning now to FIGS. 11A–11D, a laser capture microdissection (LCM) biological reaction vessel 1100 including an analysis vessel 1110 with an internal ridge and a cap 1120 with a transfer film 1130. The transfer film 1130 can include EVA and can have a stand-off rim 1150. Stand-off rim 1150 can be a 10–20 micron ridge providing a noncontact region in the center of the transfer film 1130. The cap 1120 is an integral portion of the biological reaction vessel 1100. The analysis vessel 1110 is formed to include an internal ridge 1140. The internal ridge slopes back toward an opening in the analysis vessel 1110 so as to make a tight seal with the cap 1120, even if the stand-off rim is not present. The purpose of combining the internal ridge 1140 with the stand-off rim 1150 in a single embodiment is to provide an LCM analysis vessel and film carrier that have features to facilitate a noncontact method for positioning the transfer film over the tissue sample. The LCM non-contact method reduces the probability that areas of tissue outside the focal adhesion region will be transferred. However, if the stand-off rim 1150 later comes in contact with the reaction, this advantage will be lost. The analysis vessel 1110 with this internal sealing feature allows the transfer film 1130, with stand-off rim 1150, to contact the tissue but not contact reaction fluid in the analysis vessel 1110.

The biological reaction vessel 1100 includes the cap 1120 (lid) that can be removably coupled to the analysis vessel 1110. The transfer film 1130 is attached to the clear plastic cap 1120. The transfer film 1130 can be hot cast molded to include the stand-off rim 1150 that is 10 microns thicker than the central region of the cap 1120. The stand-off rim 1150 can be termed an annular rim. The transfer film 1130 expands in the region of the focused laser beam and is able to bridge the 10 micron gap, thereby contacting the tissue and allowing transfer of a portion of the tissue to the film. This stand-off rim 1150 can be termed a standoff region and acts as a spacer elevating the central region of the transfer film 1130 above the tissue and preventing the transfer film 1130 from contacting the tissue in this central region, until the LCM laser activate the transfer film 1130. This stand-off region feature can be molded into the transfer film 1130 by pressing the transfer film 1130 onto a heated plate that contains an inverse image of this step (spacer) feature. This method replicates the feature. Such a mold could be constructed using a polished metal plate and standard chemical etching techniques. It could also be manufactured using glass or silicon substrates and chemical etching. Alternatively, a diamond lathe could be used to machine this feature onto a suitable metal substrate (e.g., copper, aluminum, steel, etc.).

The cap 1120 that seals the liquid reagent analysis vessel 1110 can be made out of inert plastic such as polypropylene or polyethylene. The analysis vessel 1110 has the internal ridge 1140 (step) that is designed to mate with and cover the annular rim of the cap 1120 providing a tight seal at this point. This seal prevents liquids in the analysis vessel 1110 from contacting the bottom surface of the rim of the cap. This design eliminates nonspecific tissue transfer since the stand-off rim 1150 is the only area of the cap 1120 that contacts the tissue (other than the desired transfer regions illuminated by the laser) and the digestion reagents in the analysis vessel 1110 never contact this region (stand-off rim 1150). The internal ridge 1140 feature in the analysis vessel can be designed with a slight angle so as to partially cut into the Transfer film 1130 providing a very tight seal similar to vacuum flange sealing techniques. A slight bulge or indentation can be molded into the barrel of the cap 1120 or into the top portion of the analysis vessel 1110 so as to provide a downward directed force and a positive seal between the cap 1120 and the analysis vessel 1110.

EXAMPLE

A specific embodiment of the present invention will now be further described by the following, nonlimiting example which will serve to illustrate in some detail various features of significance. The example is intended merely to facilitate an understanding of ways in which the present invention may be practiced and to further enable those of skill in the art to practice the present invention. Accordingly, the example should not be construed as limiting the scope of the present invention.

In an exemplary embodiment of the invention, a glass microscope slide is first cleaned. Then the glass microscope slide is spray coated with a thin layer of a commercially available silicone release agent, in this example a silicone containing surfactant that is readily commercially available (i.e., RAINEX). Meanwhile, a supply of sample carriers in the form of microcentrifuge tube caps are molded from plexiglass G. Cylindrical chips of LCM film punched from a sheet of ethylene vinyl acetate (EVA) are then attached to the bottom surface of the caps, optionally with an epoxy adhesive. The resultant cap subassemblies are then placed on top of the release agent coated glass subassembly for hot vacuum baking. The hot vacuum baking is carried out at a pressure of approximately one torr or less at a temperature of 95° C. for approximately one hour. This planarizes the transfer film. The baked assembly is then allowed to cool to room temperature. The resulting assembly can include a planoconcave void located between each of the caps and the underlying plate. In this way only the perimeter of the bottom of the caps is in contact with the glass plate. This provides two significant advantages. First, the working surface of the LCM film is spaced apart from the glass slide in a vacuum and remains free of surface damage and contaminants. Second, the removal of each cap from the glass slide is facilitated by the fact that only a fraction of the surface area of the bottom of the cap is attached to the release layer that has been coated on the glass slide. Therefore, removal of the cap from the slide requires much less force than if the entire lower surface of the cap were in contact with the release layer.

It can be appreciated that by both making and shipping the cap on the same glass slide, the number of processing and packaging steps is reduced while reproducibility and cleanliness are improved.

The completed consumable products can be sterilized (e.g., with beta or gamma radiation). Finally, the completed consumable products should be subjected to a rigorous quality assurance inspection.

There are a number of advantages to leaving the caps on the slide until they are about to be used. These advantages include protection of the optically flat surface. For example, leaving the caps on the slide reduces hydroxyl contamination of the transfer film. These advantages also include the prevention of particulate matter from settling on the surface.

Practical Applications of the Invention

A practical application of the present invention that has value within the technological arts is the collection of a large database of gene expression patterns of both healthy and diseased tissue, at different stages of diseases. This database will be used to more fully understand that pathogenesis of cancer and infectious diseases. The present invention will enable a scientist to identify gene patterns and incorporate this information into effective diagnostics for disease. The present invention will allow medical doctors to compare actual patient tissue samples with archived data from patient samples at different disease stages, thereby allowing them to prescribe more effective stage therapies, eliminate unnecessary procedures, and reduce patient suffering. Other research areas where the present invention will find use are drug discovery, developmental biology, forensics, botany, and the study of infectious diseases such a drug-resistant tuberculosis. There are virtually innumerable uses for the present invention, all of which need not be detailed here.

Advantages of the Invention

Laser capture microdissection, representing an embodiment of the invention can be cost effective and advantageous for at least the following reasons. The present invention will replace current methods with better technology that allows for more accurate and reproducible results. The present invention can be used to provide a low cost injection molded polymer disposable that integrates a laser capture microdissection film into the interior surface of an analysis container such as a microcentrifuge tube.

All the disclosed embodiments of the invention described herein can be realized and practiced without undue experimentation. Although the best mode of carrying out the invention contemplated by the inventors is disclosed above, practice of the present invention is not limited thereto. It will be manifest that various additions, modifications and rearrangements of the features of the present invention may be made without deviating from the spirit and scope of the underlying inventive concept. Accordingly, it will be appreciated by those skilled in the art that the invention may be practiced otherwise than as specifically described herein.

For example, the individual components need not be formed in the disclosed shapes, or assembled in the disclosed configuration, but could be provided in virtually any shape, and assembled in virtually any configuration. Further, the individual components need not be fabricated from the disclosed materials, but could be fabricated from virtually any suitable materials. Further, although the caps and cap assemblies disclosed herein are described as a physically separate module, it will be manifest that the caps and cap assemblies may be integrated into other apparatus with which they are associated. Furthermore, all the disclosed elements and features of each disclosed embodiment can be combined with, or substituted for, the disclosed elements and features of every other disclosed embodiment except where such elements or features are mutually exclusive.

It is intended that the appended claims cover all such additions, modifications and rearrangements. The claims are not to be construed as including means-plus-function limitations, unless such limitations are explicitly recited using the term "means" in the claims. Expedient embodiments of the present invention are differentiated by the appended subclaims.

What is claimed is:

1. An apparatus, comprising:
a transfer film carrier having a substrate surface; and
a laser capture microdissection transfer film coupled to said substrate surface of said transfer film carrier, said laser capture microdissection transfer film including at least one integrally formed structural feature that protrudes and provides a controllable spacing between said laser capture microdissection transfer film and a sample.

2. The apparatus of claim 1, wherein said laser capture microdissection transfer film includes a material, that upon exposure to sufficient electromagnetic energy, expands and projects itself away from said substrate surface.

3. The apparatus of claim 1, further comprising a scattering media in proximity to said laser capture microdissection transfer film.

4. The apparatus of claim 1, wherein said laser capture microdissection transfer film includes an absorptive substance.

5. The apparatus of claim 1, wherein said laser capture microdissection transfer film is hot vacuum baked onto said substrate surface.

6. The apparatus of claim 1, wherein said laser capture microdissection transfer film is bonded to said substrate surface with a refractive index matching transparent glue.

7. The apparatus of claim 1, wherein said transfer film carrier includes a negative draft such that a distal diameter defined by said surface of said transfer film carrier is greater than a proximal diameter defined by an inner perimeter of said transfer film carrier.

8. The apparatus of claim 7, wherein said transfer film carrier includes a girdle that is contiguous with said negative draft.

9. The apparatus of claim 7, wherein said transfer film carrier includes a chamfer that is contiguous with said substrate surface.

10. The apparatus of claim 1, wherein said laser capture microdissection transfer film has a thickness that is less than 500 microns.

11. The apparatus of claim 1, wherein said laser capture microdissection transfer film has a thickness that is held to within 20% of a given value.

12. The apparatus of claim 1, wherein said laser capture microdissection transfer film has a capture surface that is opposite said substrate surface, said capture surface having a flatness that is held within five microns.

13. The apparatus of claim 1, wherein said laser capture microdissection transfer film includes at least one pedestal that protrudes and defines a laser capture microdissection acquisition zone.

14. The apparatus of claim 1, wherein said laser capture microdissection transfer film includes a protruding feature that runs along at least three points of a perimeter of said laser capture microdissection transfer film.

15. A microcentrifuge tube cap, comprising:
a transfer film carrier having a substrate surface; and
a laser capture microdissection transfer film coupled to said substrate surface of said transfer film carrier, said laser capture microdissection transfer film including at least one integrally formed structural feature that protrudes and provides a controllable spacing between said laser capture microdissection transfer film and a sample.

16. An integral portion of a biological reaction vessel, comprising:
a transfer film carrier having a substrate surface; and
a laser capture microdissection transfer film coupled to said substrate surface of said transfer film carrier, wherein said laser capture microdissection transfer film includes at least one integrally formed structural feature that protrudes and provides a controllable spacing between said laser capture microdissection transfer film and a sample.

17. The integral portion of a biological reaction vessel according to claim 16, wherein said laser capture microdissection transfer film includes a material, that upon exposure to sufficient electromagnetic energy, expands and projects itself away from said substrate surface.

18. The integral portion of a biological reaction vessel according to claim 16, further comprising a scattering media in proximity to said laser capture microdissection transfer film.

19. The integral portion of a biological reaction vessel according to claim 16, wherein said laser capture microdissection transfer film includes an absorptive substance.

20. The integral portion of a biological reaction vessel according to claim 16, wherein said laser capture microdissection transfer film is hot vacuum baked onto said substrate surface.

21. The integral portion of a biological reaction vessel according to claim 16, wherein said laser capture microdissection transfer film is bonded to said substrate surface with a refractive index matching transparent glue.

22. The integral portion of a biological reaction vessel according to claims 16, wherein said transfer film carrier includes a negative draft such that a distal diameter defined by said surface of said transfer film carrier is greater than a proximal diameter defined by an inner perimeter of said transfer film carrier.

23. The integral portion of a biological reaction vessel according to claim 22, wherein said transfer film carrier includes a girdle that is contiguous with said negative draft.

24. The integral portion of a biological reaction vessel according to claim 22, wherein said transfer film carrier includes a chamfer that is contiguous with said substrate surface.

25. The integral portion of a biological reaction vessel according to claim 16, wherein said laser capture microdissection transfer film has a thickness that is less than 500 microns.

26. The integral portion of a biological reaction vessel according to claim 16, wherein said laser capture microdissection transfer film has a thickness that is held to within 20% of a given value.

27. The integral portion of a biological reaction vessel according to claim 16, wherein said laser capture microdissection transfer film has a surface opposite said substrate surface having a flatness that is held within five microns.

28. The integral portion of a biological reaction vessel according to claim 16, wherein said laser capture microdissection transfer film includes at least one pedestal that protrudes and defines a laser capture microdissection acquisition zone.

29. The integral portion of a biological reaction vessel according to claim 16, wherein said laser capture microdissection transfer film includes a protruding feature that runs along at least three points of a perimeter of said laser capture microdissection transfer film.

30. A microcentrifuge tube cap, comprising an integral portion of a biological reaction vessel including:
   a transfer film carrier having a substrate surface; and
   a laser capture microdissection transfer film coupled to said substrate surface of said transfer film carrier, wherein said laser capture microdissection transfer film includes at least one integrally formed structural feature that protrudes and provides a controllable spacing between said laser capture microdissection transfer film and a sample.

31. A laser capture microdissection assembly comprising:
   a plate having a top surface; and
   at least one laser capture microdissection cap coupled to said top surface of said plate, wherein said at least one laser capture microdissection cap includes:
      a transfer film carrier having a substrate surface; and
      a laser capture microdissection transfer film coupled to said substrate surface of said transfer film carrier, wherein said laser capture microdissection transfer film includes at least one integrally formed structural feature that protrudes and provides a controllable space in between said laser capture microdissection transfer film and a sample.

32. The laser capture microdissection assembly of claim 31, further comprising a release layer coated on said plate, said release layer being located between said plate and said laser capture microdissection transfer film of each of said at least one laser capture microdissection cap.

33. The laser capture microdissection assembly of claim 32, wherein said release layer includes at least one nonadhesive material selected from the group consisting of silicones and polytetrafluoroethylenes.

34. The laser capture microdissection assembly of claim 33, wherein said at least one nonadhesive material is a silicone containing surfactant agent.

35. The laser capture microdissection assembly of claim 31, wherein a plano-concave void is located between said laser capture microdissection transfer film of said at least one laser capture microdissection cap and said top surface of said plate.

36. The laser capture microdissection assembly of claim 31, wherein said laser capture microdissection transfer film includes a transparent thermoplastic.

37. The laser capture microdissection assembly of claim 31, wherein said laser capture microdissection transfer film includes an absorptive substance.

38. The laser capture microdissection assembly of claim 31, wherein said laser capture microdissection transfer film is hot vacuum baked onto said substrate surface.

39. The laser capture microdissection assembly of claim 31, wherein said transfer film carrier includes a negative draft such that a distal diameter defined by said surface of said transfer film carrier is greater than a proximal diameter defined by an inner perimeter of said transfer film carrier.

40. The laser capture microdissection assembly of claim 31, wherein said laser capture microdissection transfer film has a thickness that is less than 500 microns.

41. The laser capture microdissection assembly of claim 31, wherein said laser capture microdissection transfer film has a thickness that is held to within 20% of a given value.

42. The laser capture microdissection assembly of claim 31, wherein said laser capture microdissection transfer film has a surface opposite said substrate surface having a flatness that is held within five microns.

43. The laser capture microdissection assembly of claim 31, further comprising at least one diffuser coupled to said at least one transfer film carrier.

44. A set of microcentrifuge tube caps, comprising a laser capture microdissection assembly including:
   a plate having a top surface; and
   at least one laser capture microdissection cap coupled to said top surface of said plate, wherein said at least one laser capture microdissection cap includes:
      a transfer film carrier having a substrate surface; and
      a laser capture microdissection transfer film coupled to said substrate surface of said transfer film carrier, wherein said laser capture microdissection transfer film includes at least one integrally formed structural feature that protrudes and provides a controllable space in between said laser capture microdissection transfer film and a sample.

45. An apparatus comprising:
   a transfer film carrier having a substrate surface; and
   a laser capture microdissection transfer film coupled to said substrate surface of said transfer film carrier wherein said transfer film carrier is adapted to cap a vessel such that at least a portion of said transfer film is disposed inside said vessel.

46. The apparatus according to claim 45, wherein said laser capture microdissection transfer film includes a material, that upon exposure to sufficient electromagnetic energy, expands and projects itself away from said substrate surface.

47. The apparatus according to claim 45, further comprising a scattering media in proximity to said laser capture microdissection transfer film.

48. The apparatus according to claim 45, wherein said laser capture microdissection transfer film includes a base material and an absorptive substance.

49. The apparatus according to claim 45, wherein said laser capture microdissection transfer film is hot vacuum baked onto said substrate surface.

50. The apparatus according to claim 45, wherein said laser capture microdissection transfer film is bonded to said substrate surface with a refractive index matching transparent glue.

51. The apparatus according to claim 45, wherein said transfer film carrier includes a negative draft such that a distal diameter defined by said surface of said transfer film carrier is greater than a proximal diameter defined by an inner perimeter of said transfer film carrier.

52. The apparatus according to claim 51, wherein said transfer film carrier includes a girdle that is contiguous with said negative draft.

53. The apparatus according to claim 51, wherein said transfer film carrier includes a chamfer that is contiguous with said substrate surface.

54. The apparatus according to claim 45, wherein said laser capture microdissection transfer film has a thickness that is less than 500 microns.

55. The apparatus according to claim 45, wherein said laser capture microdissection transfer film has a thickness that is held to within 20% of a given value.

56. The apparatus according to claim 45, wherein said laser capture microdissection transfer film has a surface opposite said substrate surface having a flatness that is held within five microns.

57. The apparatus according to claim 45 further including a sealing feature that excludes a portion of said transfer film carrier from the interior of said vessel.

58. The apparatus according to claim 45 wherein said vessel includes an internal ridge adapted to contact a portion of said transfer film carrier.

59. The apparatus according to claim 58 wherein said transfer film carrier includes at least one stand-off; and the portion of the carrier contacted by said internal ridge of the vessel includes said at least one stand-off.

60. An apparatus comprising:
a transfer film carrier having a substrate surface; and
a laser capture microdissection transfer film coupled to said substrate surface of said transfer film carrier wherein said transfer film carrier is adapted to be coupled to a vessel such that at least a portion of said transfer film is disposed inside said vessel; and
wherein said laser capture microdissection transfer film includes at least one pedestal that protrudes and defines a laser capture microdissection acquisition zone.

61. An apparatus comprising:
a transfer film carrier having a substrate surface; and
a laser capture microdissection transfer film coupled to said substrate surface of said transfer film carrier wherein said transfer film carrier is adapted to be coupled to a vessel such that at least a portion of said transfer film is disposed inside said vessel; and
wherein said laser capture microdissection transfer film includes a protruding feature that runs along at least three points of a perimeter of said laser capture microdissection transfer film.

62. An apparatus comprising:
a transfer film carrier having a substrate surface, and
a laser capture microdissection transfer film coupled to said substrate surface of said transfer film carrier wherein said transfer film carrier is adapted to cap a microcentrifuge tube such that at least a portion of said transfer film is disposed inside said microcentrifuge tube.

63. A laser capture microdissection assembly comprising:
a plate having a top surface; and
at least one laser capture microdissection cap coupled to said top surface of said plate, wherein said at least one laser capture microdissection cap includes
a transfer film carrier having a substrate surface; and
a laser capture microdissection transfer film coupled to said substrate surface of said transfer film carrier.

64. The laser capture microdissection assembly of claim 63, further comprising a release layer coated on said plate, said release layer being located between said plate and said laser capture microdissection transfer film of each of said at least one laser capture microdissection cap.

65. The laser capture microdissection assembly of claim 64, wherein said release layer includes at least one nonadhesive material selected from the group consisting of silicones and polytetrafluoroethylenes.

66. The laser capture microdissection assembly of claim 65, wherein said at least one nonadhesive material is a silicone containing surfactant agent.

67. The laser capture microdissection assembly of claim 63, wherein a plano-concave void is located between said laser capture microdissection transfer film of said at least one laser capture microdissection cap and said top surface of said plate.

68. The laser capture microdissection assembly of claim 63, wherein said laser capture microdissection transfer film includes a transparent thermoplastic.

69. The laser capture microdissection assembly of claim 63, wherein said laser capture microdissection transfer film includes an absorptive substance.

70. The laser capture microdissection assembly of claim 63, wherein said laser capture microdissection transfer film is hot vacuum baked onto said substrate surface.

71. The laser capture microdissection assembly of claim 63, wherein said transfer film carrier includes a negative draft such that a distal diameter defined by said surface of said transfer film carrier is greater than a proximal diameter defined by an inner perimeter of said transfer film carrier.

72. The laser capture microdissection assembly of claim 63, wherein said laser capture microdissection transfer film has a thickness that is less than 500 microns.

73. The laser capture microdissection assembly of claim 63, wherein said laser capture microdissection transfer film has a thickness that is held to within 20% of a given value.

74. The laser capture microdissection assembly of claim 63, wherein said laser capture microdissection transfer film has a surface opposite said substrate surface having a flatness that is held within five microns.

75. The laser capture microdissection assembly of claim 63, further comprising at least one diffuser coupled to said at least one transfer film carrier.

76. A set of microcentrifuge tube caps, comprising a laser capture microdissection assembly including:
a plate having a top surface; and
at least one laser capture microdissection cap coupled to said top surface of said plate, wherein said at least one laser capture microdissection cap includes
a transfer film carrier having a substrate surface, and
a laser capture microdissection transfer film coupled to said substrate surface of said transfer film carrier.

* * * * *